(12) United States Patent
Ingham

(10) Patent No.: US 11,771,627 B2
(45) Date of Patent: Oct. 3, 2023

(54) AROMATIC SHOWER SACHET

(71) Applicant: Kimberly Anne Ingham, Colorado Springs, CO (US)

(72) Inventor: Kimberly Anne Ingham, Colorado Springs, CO (US)

( * ) Notice: Subject to any disclaimer, the term of this patent is extended or adjusted under 35 U.S.C. 154(b) by 261 days.

(21) Appl. No.: 17/401,282

(22) Filed: Aug. 12, 2021

(65) Prior Publication Data

US 2022/0047467 A1  Feb. 17, 2022

Related U.S. Application Data

(60) Provisional application No. 63/064,800, filed on Aug. 12, 2020.

(51) Int. Cl.
| | |
|---|---|
| *A61K 8/02* | (2006.01) |
| *A61L 9/013* | (2006.01) |
| *B01J 31/04* | (2006.01) |
| *A61K 8/73* | (2006.01) |
| *A61K 8/365* | (2006.01) |
| *A61K 8/92* | (2006.01) |
| *A61K 8/19* | (2006.01) |
| *A61Q 13/00* | (2006.01) |

(52) U.S. Cl.
CPC .............. *A61K 8/0204* (2013.01); *A61K 8/19* (2013.01); *A61K 8/365* (2013.01); *A61K 8/732* (2013.01); *A61K 8/922* (2013.01); *A61L 9/013* (2013.01); *B01J 31/04* (2013.01); *A61L 2209/131* (2013.01); *A61L 2209/15* (2013.01); *A61Q 13/00* (2013.01)

(58) Field of Classification Search
None
See application file for complete search history.

(56) References Cited

U.S. PATENT DOCUMENTS

| | | |
|---|---|---|
| 6,289,967 B1 | 9/2001 | Moore |
| 6,906,017 B1 | 6/2005 | Pak et al. |
| 7,761,936 B2 | 7/2010 | White |
| 9,783,325 B1 | 10/2017 | Hierholzer |
| 2010/0040774 A1 | 2/2010 | Russell |

OTHER PUBLICATIONS

Beauty-N-Craft, Peppermint, Rose, Rosemary, Aromatherapy Clarity, Energy Shower Steam Bags, ebay.com, May 2020.

*Primary Examiner* — Nannette Holloman

(57) ABSTRACT

An aromatic shower sachet is a personal hygiene and aromatherapy device used to diffuse pleasant and therapeutic scents throughout a shower area when exposed to water or steam. The aromatic shower sachet utilizes a permeable enclosure containing a quantity of aromatic compound, a quantity of absorbent starch, a quantity of reactive base, and a quantity of acid catalyst homogenously mixed into water-reactive mixture. The water-reactive mixture is retained within the permeable enclosure such that water or water vapor may penetrate the permeable enclosure. The water reacts on-contact with the water-reactive mixture, releasing fragrances through the permeable enclosure.

20 Claims, 7 Drawing Sheets

AROMATIC SHOWER SACHET

The current application claims a priority to the U.S. Provisional Patent application Ser. No. 63/064,800 filed on Aug. 12, 2020.

FIELD OF THE INVENTION

The present invention generally relates to bathroom products and aromatherapy devices. More specifically, the present invention provides a water-reactive device configured to create a therapeutic, spa-like experience in a shower.

BACKGROUND OF THE INVENTION

Aromatic compounds and odorant devices can be used to create a therapeutic and spa-like experience while in the shower using aromatherapy. The shower steamer sachet can be placed at the bottom of the shower or hanged from an object somewhere in the shower where water will hit the shower steamer sachet. However, the shower steamer sachet is preferably hung and not placed on the ground so more fragrance can be added to the shower steamer sachet without worrying about the floor becoming too slick. When water hits the shower steamer sachet, aroma is released throughout the shower. The shower steamer sachet eliminates any possible mess by containing the aromatherapy mixture inside a sealable container made from porous materials that enable water flow into the sachet and aroma flow out of the sachet. Further, since the shower steamer sachet can be hung, the shower steamer sachet is not always drenched in water which also increases the shower steamer sachet's lifetime. Thus, no aromatherapy mixture ingredients will be washed down the drain into the wastewater infrastructure while being able to provide a long-lasting aromatherapy spa experience, two to three times longer than other currently available shower steamers. The shower steamer sachet can also be designed to be used multiple times by enabling the replacement of the aromatherapy mixture.

The aromatherapy mixture of the shower steamer sachet preferably includes, but is not limited to, sodium bicarbonate, tapioca starch (e.g., Natrasorb), various essential oils, various fragrance oils, and different body safe colorants. The aromatherapy mixture ingredients are mixed, and a specific weight of the mixture is added to the shower steamer sachet. The shower steamer sachet can then be sealed, either permanently or resealable, for use. The shower steamer sachet can be permanently sealed using different sealing techniques such as heat sealing. The shower steamer sachet can also be made resealable using different sealing fasteners, such as snap-sealing fasteners. The shower steamer sachet can then be packaged and labeled.

Additional advantages of the invention will be set forth in part in the description which follows, and in part will be obvious from the description, or may be learned by practice of the invention. Additional advantages of the invention may be realized and attained by means of the instrumentalities and combinations particularly pointed out in the detailed description of the invention section. Further benefits and advantages of the embodiments of the invention will become apparent from consideration of the following detailed description given with reference to the accompanying drawings, which specify and show preferred embodiments of the present invention.

DETAIL DESCRIPTIONS OF THE INVENTION

Figure 1:
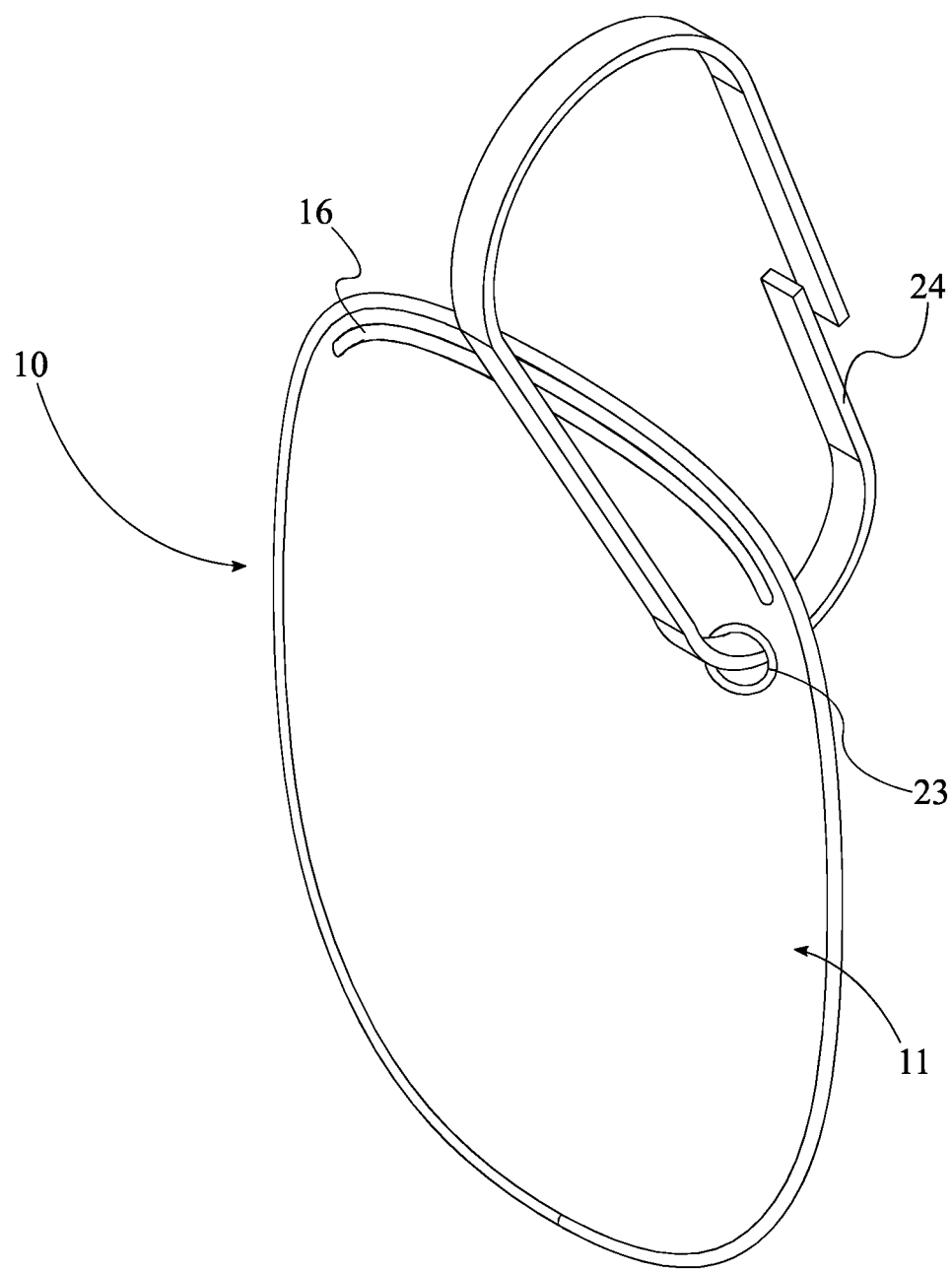
FIG. 1 is a top-front-left perspective view of one embodiment of the present invention, wherein an exemplary hanging assembly is utilized.

All illustrations of the drawings are for the purpose of describing selected versions of the present invention and are not intended to limit the scope of the present invention. The present invention is to be described in detail and is provided in a manner that establishes a thorough understanding of the present invention. There may be aspects of the present invention that may be practiced or utilized without the implementation of some features as they are described. It should be understood that some details have not been described in detail in order to not unnecessarily obscure focus of the invention. References herein to "the preferred embodiment", "one embodiment", "some embodiments", or "alternative embodiments" should be considered to be illustrating aspects of the present invention that may potentially vary in some instances, and should not be considered to be limiting to the scope of the present invention as a whole.

In reference to FIG. 1 through 7, the present invention is an aromatic shower sachet comprising a permeable enclosure 10, a quantity of aromatic compound 30, a quantity of absorbent starch 29, a quantity of reactive base 27, and a quantity of acid catalyst 28.

Figure 6:
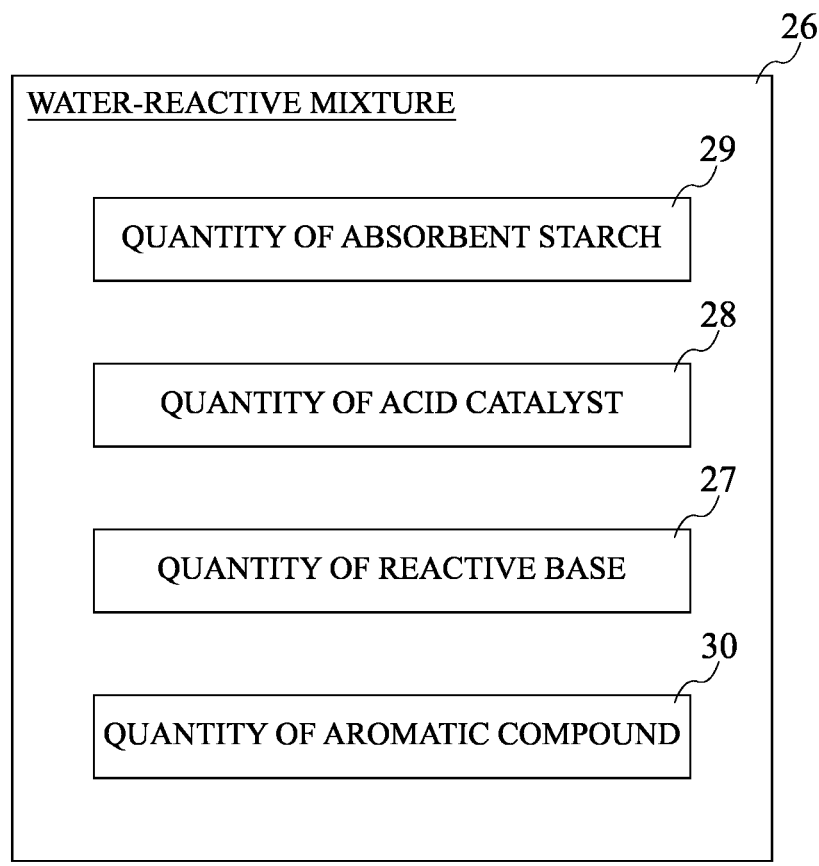
FIG. 6 is a block diagram of the constituent ingredients for a water-reactive mixture.

In reference to FIG. 6, the quantity of aromatic compound 30, the quantity of absorbent starch 29, the quantity of reactive base 27, and the quantity of acid catalyst 28 are homogeneously mixed into a water-reactive mixture 26. The water-reactive mixture 26 constitutes a generally anhydrous composition configured to progressively dissolve into a semi-fluid or slurry, thereby releasing the active ingredients contained within the quantity of aromatic compound 30. The water-reactive mixture 26 is retained within the permeable enclosure 10 to prevent a fluidized form of the water-reactive mixture 26 from sloughing down a drain or otherwise wasting the undissolved portions of the water-reactive mixture 26 before the quantity of aromatic compound 30 therein is fully diffused.

The quantity of absorbent starch 29 constitutes a dry binder compound or similar retentive material suitable for encapsulating and preserving the quantity of aromatic compound 30 within the water-reactive mixture 26. Accordingly, the quantity of absorbent starch 29 is configured to expose and separate from the quantity of aromatic compound 30 when exposed to moisture and heat, i.e., steam in a shower or bath.

The quantity of acid catalyst 28 and the quantity of reactive base 27 are broadly defined as any opposing pair of stable compounds of greater and lesser chemical acidity on the pH scale, respectively. The physical combination of the quantity of acid catalyst 28 and the quantity of reactive base 27 are insufficient to cause a normalizing reaction between these elements, but the addition of heat or solvent (i.e., water) ideally causes the quantity of acid catalyst 28 and the quantity of reactive base 27 to undergo a normalizing reaction, wherein the reaction serves to accelerate the diffusion of the quantity of aromatic compound 30 through the permeable enclosure 10 and into a surrounding area.

Figure 7:
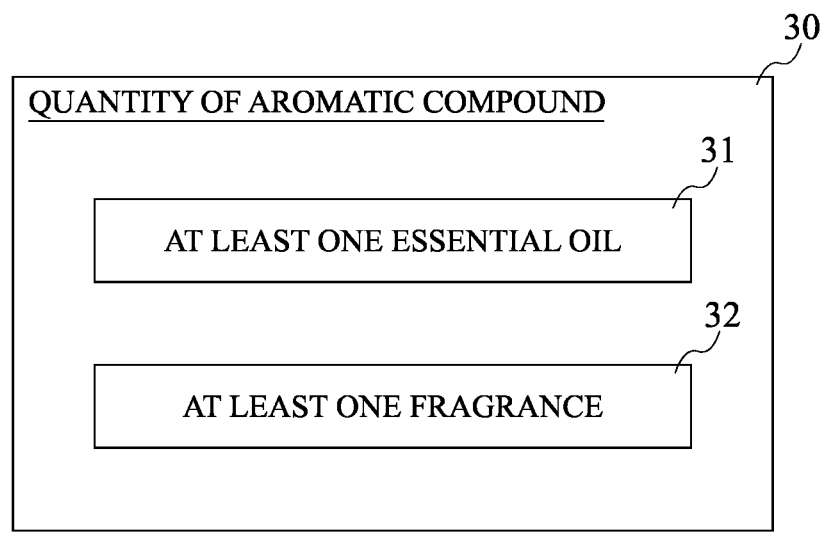
FIG. 7 is a block diagram of the sub-components of a quantity of aromatic compound.

As indicated in FIG. 7, the quantity of aromatic compound 30 is further defined as a mixture of various disparate elements. The quantity of aromatic compound 30 is selected from a group consisting of: at least one essential oil 31, at least one fragrance 32, and combinations thereof. The combination of these elements provides a means for any individual user to tailor each instance of the present invention towards a variety of given use-cases and individual tastes. In at least one conceivable application of the present invention, the quantity of aromatic compound 30 is adjusted to include at least one pharmacologically active compound, at least one therapeutic compound, at least one psychoactive compound, or combinations thereof throughout a course of aromatherapy treatment.

The at least one essential oil 31 generally refers to any liquid or semi-liquid composition capable of producing some therapeutic effect once aerosolized of vaporized. In a broader context, the at least one essential oil 31 may be prepared into a crystalline form or binder prior to inclusion in the quantity of aromatic compound 30. For example, crystalline menthol may be readily added to any given embodiment to produce a decongestant or mild analgesic effect once dissolves, while menthol oils would produce an equivalent effect utilizing an identical active ingredient in a different format. Likewise, the at least one fragrance 32 may be interchanged or combined with any fragrant element to achieve a preferred aroma without departing from the original spirit and scope of the present invention. In all recombination proposes herein, the quantity of aromatic compound 30 is approximately between 1 to 10 percentage by weight (wt. %) of the water-reactive mixture 26.

The quantity of absorbent starch 29 is preferably a tapioca-based starch, provided that the tapioca base is generally safe for use for all persons and will not strongly conflict aromatically with any other active ingredients of the present invention. The quantity of absorbent starch 29 is approximately between 1 to 10 wt. % of the water-reactive mixture 26, corresponding to the quantity of aromatic compound 30 that is retained therein.

The quantity of reactive base 27 is preferably sodium bicarbonate, selected for the controllable reactivity with the quantity of acid catalyst 28. Further, sodium bicarbonate may be used to retain any excess amounts of the quantity of aromatic compound 30 exceeding the retentive capacity of the quantity of absorbent starch 29. The quantity of reactive base 27 is approximately between 40 to 90 wt. % of the water-reactive mixture 26.

The quantity of acid catalyst 28 is preferably citric acid. Natural sources of citric acid provide citrus fragrance in addition to the acid reactivity required to effectively catalyze a reaction with the quantity of reactive base 27. The quantity of acid catalyst 28 is approximately between 3 to 10 wt. % of the water-reactive mixture 26.

In the regular use of the present invention, the permeable enclosure 10 is required to contain the water-reactive mixture 26 throughout exposure to heat, moisture, and general handling without breaching or tearing. Failure of the permeable enclosure 10 at any point would allow the water-retentive mixture to leak outward, preventing the effective diffusion of the quantity of aromatic compound 30. In reference to FIG. 5, the permeable enclosure 10 further comprises a porous layer 12 and a perforated tensile layer 13 in at least one embodiment. The perforated tensile layer 13 is superimposed onto the porous layer 12. The porous layer 12, being suitably thin to allow moisture permeation, is identified as the most-likely point of failure for the permeable enclosure 10. Accordingly, the perforated tensile layer 13 externally encloses and protects the porous layer 12. This arrangement ensures that any external damage is exerted against the perforated tensile layer 13, while the porous layer 12 remains substantially exposed to the surrounding atmosphere to enable the diffusion of the quantity of aromatic compound 30 therein.

Figure 2:
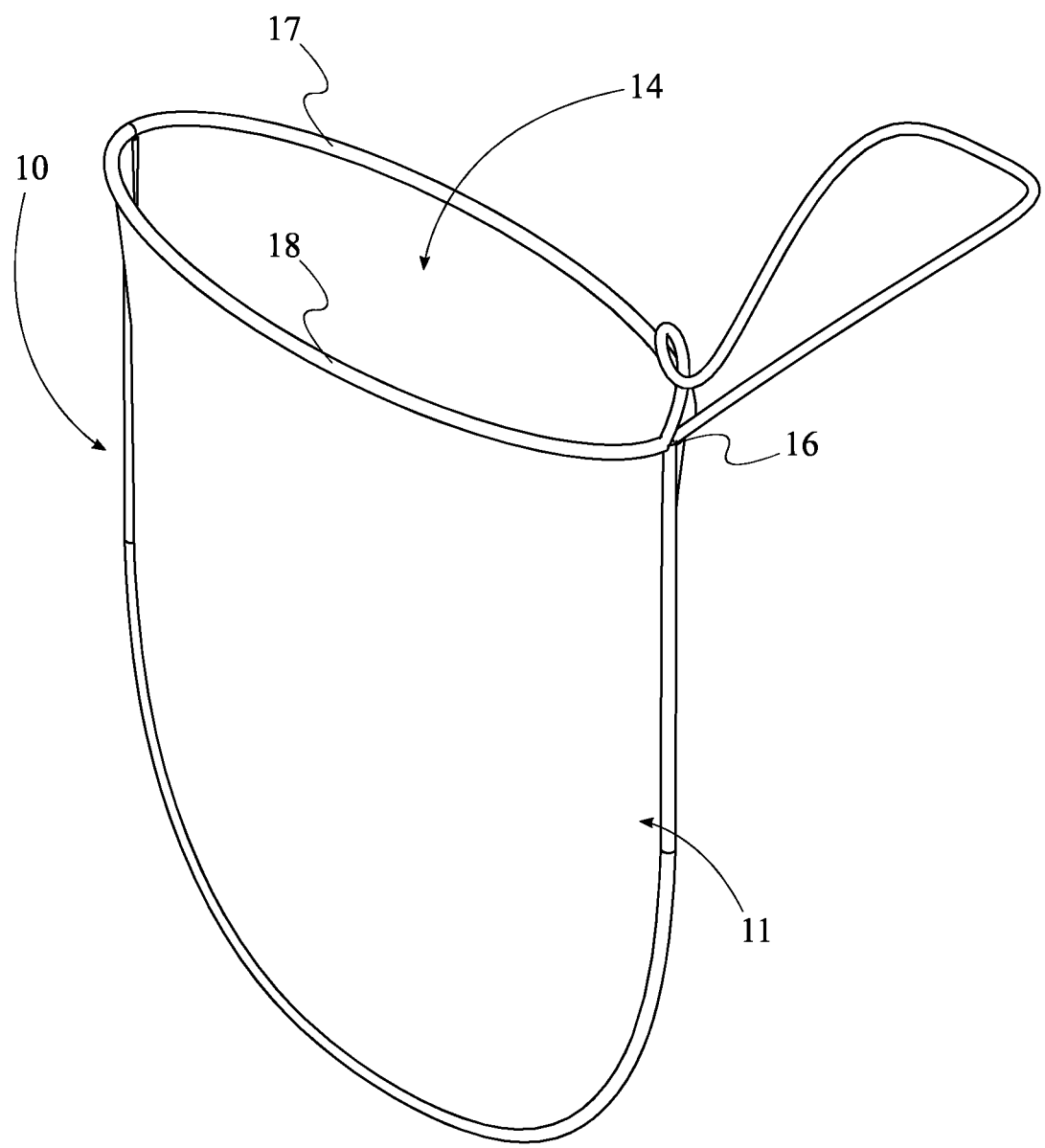
FIG. 2 is a perspective view of an alternate embodiment of the present invention.
Figure 3:
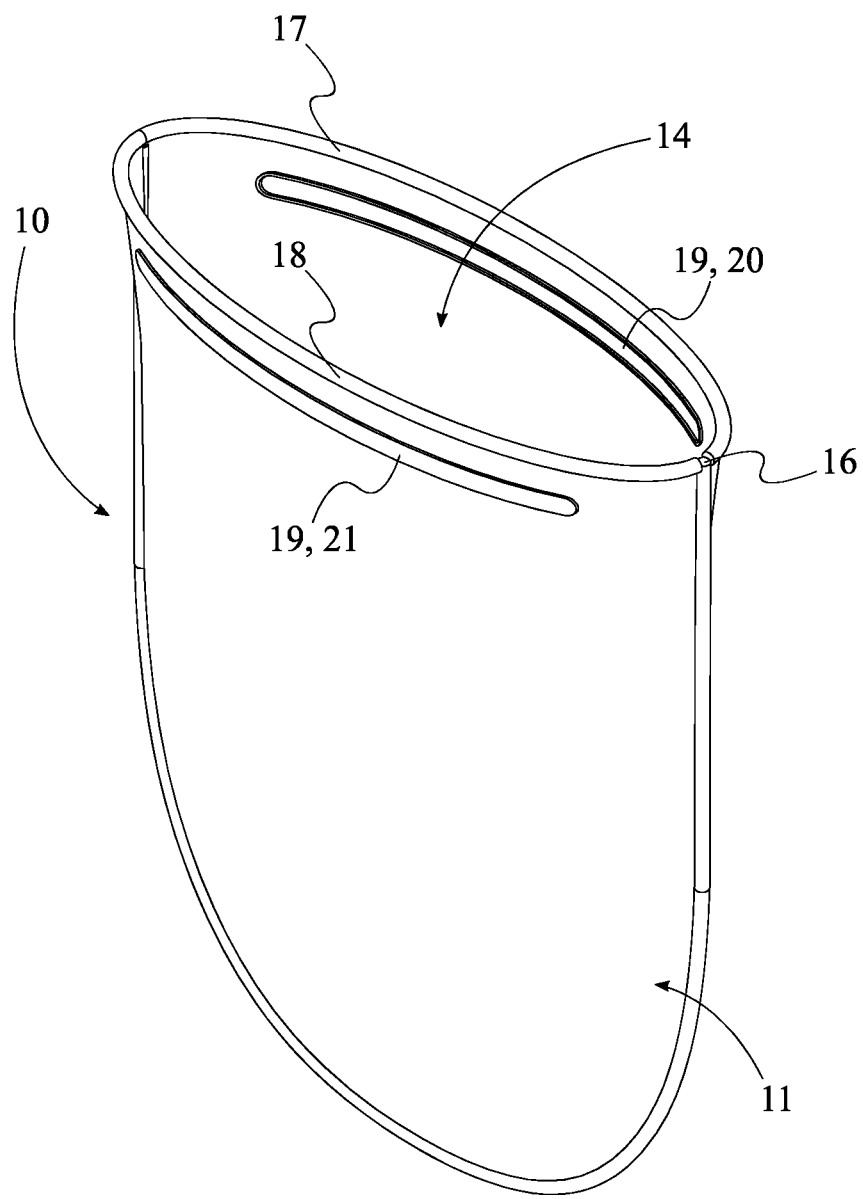
FIG. 3 is a perspective view of another alternate embodiment of the present invention, wherein the invention is depicted open to show construction.
Figure 4:
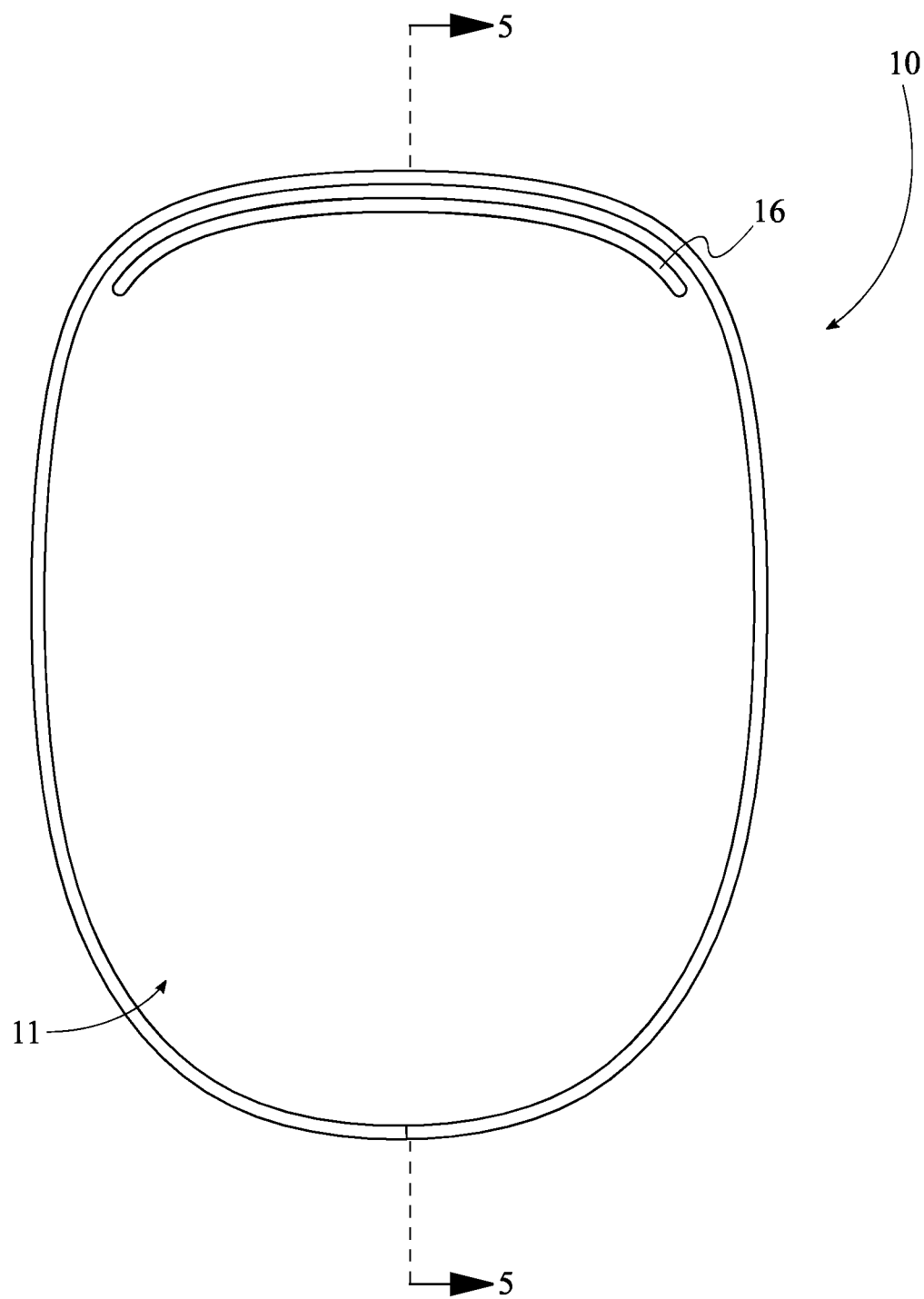
FIG. 4 is a front elevational view of a simplified embodiment of the present invention.
Figure 5:
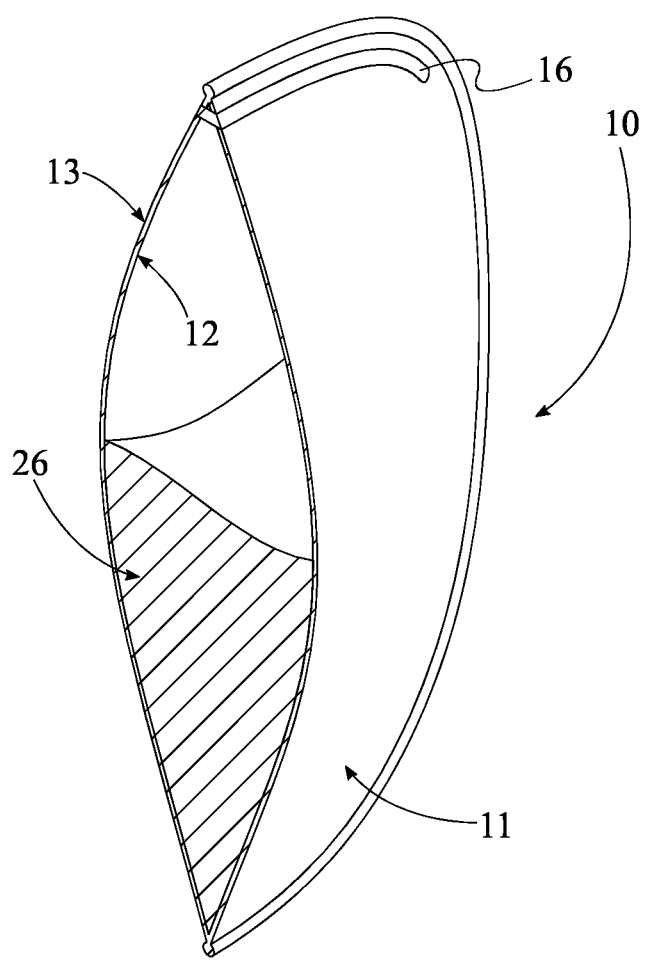
FIG. 5 is a section view of taken along line 5-5 in FIG. 4.

It is further recognized that the permeable enclosure 10 must be loaded with the water-reactive mixture 26, therefore a means to access the interior of the permeable enclosure 10 must be provided. As shown in FIGS. 3 and 4, one embodiment of the permeable enclosure 10 comprises an enclosure body 11, at least one aperture 14, and at least one seam 16. The at least one aperture 14 traverses into the enclosure body 11, wherein the at least one aperture 14 delineates a first aperture edge 17 of the enclosure body 11 and a second aperture edge 18 of the enclosure body 11. The first aperture edge 17 is attached along the second aperture edge 18 by the at least one seam 16, wherein the at least one seam 16 defines any linear self-attachment means formed into the permeable enclosure 10. In one embodiment, the first aperture edge 17 and the second aperture edge 18 are stitched together, wherein the at least one seam 16 defines the stitched line formed therethrough. In another embodiment, the at least one seam 16 constitutes a thermal or chemical weldment formed into the enclosure body 11 to combine the first aperture edge 17 and the second aperture edge 18. In yet another embodiment, the at least one seam 16 may define a continuous sleeve formed across both the first aperture edge 17 and the second aperture edge 18, wherein a drawstring or cable may be drawn to constrict and close the aperture into the enclosure body 11 as shown in FIG. 2.

It is further proposed that the permeable enclosure 10 be configured for reuse or reloading, wherein an alternate embodiment of the permeable enclosure 10 comprises the enclosure body 11, at least one aperture 14, and at least one fastener 19 as shown in exemplary form in FIG. 3. The at least one fastener 19 further comprises a first interlocking piece 20 and a second interlocking piece 21, wherein the first interlocking piece 20 and the second interlocking piece 21 broadly define releasable mechanical fasteners of any type, variety, or combination. As in the embodiment outlined above, the at least one aperture 14 traverses into the enclosure body 11 and the at least one aperture 14 delineates a first aperture edge 17 of the enclosure body 11, and a second aperture edge 18 of the enclosure body 11. The first interlocking piece 20 is connected along the first aperture edge 17, and the second interlocking piece 21 is connected along the second aperture edge 18, with each component positionally corresponding to the other across the aperture. The first interlocking piece 20 and the second interlocking piece 21 are releasably engaged to each other, thereby enabling a user to access the interior of the enclosure body 11 to refresh or replace the water-reactive mixture 26 to enable extended use of the present invention.

As outlined previously, the water-reactive mixture 26 must be exposed to water or water vapor through the permeable enclosure 10 to begin diffusing the quantity of aromatic compound 30. Consequently, the volume of water or water vapor that may penetrate to the water-reactive mixture 26 is limited by the exposed surface area of the permeable enclosure 10. In reference to FIG. 1, the present invention may further comprise at least one eyelet 23 and an external hook 24. The at least one eyelet 23 is integrated into the permeable enclosure 10, and the external hook 24 is positioned through the at least one eyelet 23. The external hook 24 may be attach to a shower curtain or wall-hanger opposite the at least one eyelet 23 to enable the present invention to be hung within a shower stall or bathroom, ensuring that the permeable enclosure 10 is fully exposed to any ambient steam or moisture. Accordingly, the water-reactive mixture 26 is positioned to effectively diffuse the quantity of aromatic compound 30 therein into the surrounding atmosphere from an elevated position.

Although the invention has been explained in relation to its preferred embodiment, it is to be understood that many other possible modifications and variations can be made without departing from the spirit and scope of the invention as hereinafter claimed.

What is claimed is:

1. An aromatic shower sachet comprising:
   a permeable enclosure;
   a quantity of aromatic compound;
   a quantity of absorbent starch;
   a quantity of reactive base;
   a quantity of acid catalyst;
   the quantity of aromatic compound, the quantity of absorbent starch, the quantity of reactive base, and the quantity of acid catalyst being homogeneously mixed into a water-reactive mixture; and
   the water-reactive mixture being retained within the permeable enclosure.

2. The aromatic shower sachet as claimed in claim 1, wherein the quantity of aromatic compound is selected from a group consisting of: at least one essential oil, at least one fragrance, and combinations thereof.

3. The aromatic shower sachet as claimed in claim 1, wherein the quantity of aromatic compound is approximately between 1 to 10 percentage by weight (wt. %) of the water-reactive mixture.

4. The aromatic shower sachet as claimed in claim 1, wherein the quantity of absorbent starch is tapioca-based starch.

5. The aromatic shower sachet as claimed in claim 1, wherein the quantity of absorbent starch is approximately between 1 to 10 wt. % of the water-reactive mixture.

6. The aromatic shower sachet as claimed in claim 1, wherein the quantity of reactive base is sodium bicarbonate.

7. The aromatic shower sachet as claimed in claim 1, wherein the quantity of reactive base is approximately between 40 to 90 wt. % of the water-reactive mixture.

8. The aromatic shower sachet as claimed in claim 1, wherein the quantity of acid catalyst is citric acid.

9. The aromatic shower sachet as claimed in claim 1, wherein the quantity of acid catalyst is approximately between 3 to 10 wt. % of the water-reactive mixture.

10. The aromatic shower sachet as claimed in claim 1 comprising:
    the permeable enclosure comprising a porous layer and a perforated tensile layer; and
    the perforated tensile layer being superimposed onto the porous layer.

11. The aromatic shower sachet as claimed in claim 1 comprising:
    the permeable enclosure comprising an enclosure body, at least one aperture, and at least one seam;
    the at least one aperture traversing into the enclosure body;
    the at least one aperture delineating a first aperture edge of the enclosure body and a second aperture edge of the enclosure body; and
    the first aperture edge being attached along the second aperture edge by the at least one seam.

12. The aromatic shower sachet as claimed in claim 1 comprising:
    the permeable enclosure comprising an enclosure body, at least one aperture, and at least one fastener;
    the at least one fastener comprising a first interlocking piece and a second interlocking piece;
    the at least aperture traversing into the enclosure body;
    the at least one aperture delineating a first aperture edge of the enclosure body and a second aperture edge of the enclosure body;
    the first interlocking piece being connected along the first aperture edge;
    the second interlocking piece being connected along the second aperture edge; and
    the first interlocking piece and the second interlocking piece being releasably engaged to each other.

13. The aromatic shower sachet as claimed in claim 1 comprising:
    at least one eyelet;
    an external hook;
    the at least one eyelet being integrated into the permeable enclosure; and
    the external hook being positioned through the at least one eyelet.

14. An aromatic shower sachet comprising:
    a permeable enclosure;
    a quantity of aromatic compound;
    a quantity of absorbent starch;
    a quantity of reactive base;
    a quantity of acid catalyst;
    at least one eyelet;
    an external hook;
    the quantity of aromatic compound, the quantity of absorbent starch, the quantity of reactive base, and the quantity of acid catalyst being homogeneously mixed into a water-reactive mixture;
    the water-reactive mixture being retained within the permeable enclosure;
    the permeable enclosure comprising a porous layer and a perforated tensile layer;
    the perforated tensile layer being superimposed onto the porous layer;
    the at least one eyelet being integrated into the permeable enclosure; and
    the external hook being positioned through the at least one eyelet.

15. The aromatic shower sachet as claimed in claim 14, wherein the quantity of aromatic compound is selected from a group consisting of: at least one essential oil, at least one fragrance, and combinations thereof; and the quantity of aromatic compound is approximately between 1 to 10 percentage by weight (wt. %) of the water-reactive mixture.

16. The aromatic shower sachet as claimed in claim 14, wherein the quantity of absorbent starch is tapioca-based starch comprising approximately between 1 to 10 wt. % of the water-reactive mixture.

17. The aromatic shower sachet as claimed in claim 14, wherein the quantity of reactive base is sodium bicarbonate comprising approximately between 40 to 90 wt. % of the water-reactive mixture.

18. The aromatic shower sachet as claimed in claim 14, wherein the quantity of acid catalyst is citric acid comprising approximately between 3 to 10 wt. % of the water-reactive mixture.

19. The aromatic shower sachet as claimed in claim 14 comprising:
- the permeable enclosure comprising an enclosure body, at least one aperture, and at least one seam;
- the at least one aperture traversing into the enclosure body;
- the at least one aperture delineating a first aperture edge of the enclosure body and a second aperture edge of the enclosure body; and
- the first aperture edge being attached along the second aperture edge by the at least one seam.

20. The aromatic shower sachet as claimed in claim 14 comprising:
- the permeable enclosure comprising an enclosure body, at least one aperture, and at least one fastener;
- the at least one fastener comprising a first interlocking piece and a second interlocking piece;
- the at least aperture traversing into the enclosure body;
- the at least one aperture delineating a first aperture edge of the enclosure body and a second aperture edge of the enclosure body;
- the first interlocking piece being connected along the first aperture edge;
- the second interlocking piece being connected along the second aperture edge; and
- the first interlocking piece and the second interlocking piece being releasably engaged to each other.

\* \* \* \* \*